(12) United States Patent
Wagner

(10) Patent No.: US 8,922,773 B2
(45) Date of Patent: Dec. 30, 2014

(54) SYSTEM AND METHOD FOR ERROR CORRECTION IN A POLARIMETER

(75) Inventor: Jeff A. Wagner, Long Valley, NJ (US)

(73) Assignee: Rudolph Research Analytical Inc., Hackettstown, NJ (US)

( * ) Notice: Subject to any disclaimer, the term of this patent is extended or adjusted under 35 U.S.C. 154(b) by 390 days.

(21) Appl. No.: 13/340,071

(22) Filed: Dec. 29, 2011

(65) Prior Publication Data

US 2013/0169964 A1  Jul. 4, 2013

(51) Int. Cl.
  *G01J 4/00* (2006.01)
  *G01N 21/21* (2006.01)
(52) U.S. Cl.
  CPC .. *G01J 4/00* (2013.01); *G01N 21/21* (2013.01)
  USPC .......................................... 356/367; 356/364
(58) Field of Classification Search
  CPC ........... G01J 4/00; G01N 21/21; G02B 6/276; G02B 6/2766
  See application file for complete search history.

(56) References Cited

U.S. PATENT DOCUMENTS

| | | | |
|---|---|---|---|
| 2,976,764 A * | 3/1961 | Hyde et al. .................... | 356/367 |
| 3,016,789 A * | 1/1962 | Keston .......................... | 356/368 |
| 4,671,657 A * | 6/1987 | Calvani et al. ................ | 356/484 |
| 5,227,623 A * | 7/1993 | Heffner ......................... | 250/225 |
| 5,247,176 A * | 9/1993 | Goldstein ..................... | 356/367 |
| 6,384,916 B1 * | 5/2002 | Furtak .......................... | 356/369 |
| 6,982,789 B1 * | 1/2006 | Meyer ........................... | 356/369 |
| 2002/0176079 A1 * | 11/2002 | Mueller ........................ | 356/364 |
| 2011/0149282 A1 * | 6/2011 | Wagner ........................ | 356/364 |

* cited by examiner

*Primary Examiner* — Tarifur Chowdhury
*Assistant Examiner* — Juan D Valentin, II
(74) *Attorney, Agent, or Firm* — Kaplan Breyer Schwarz & Ottesen, LLP

(57) ABSTRACT

A system and method for polarimetry are disclosed in which a polarimeter may include a light source for transmitting a light beam through a sample within a container; a wavelength selector configured to specify a target wavelength at which the polarization rotation of the light beam emerging from the sample will be evaluated; a polarization rotator configured to be selectively moved into and out of a path of the light beam from the light source; and a detector for obtaining a first measurement of the light beam polarization rotation with the polarization rotator outside the path of the light beam, and a second measurement of the light beam polarization rotation with the polarization rotator within the path of the light beam, with both measurements occurring at the wavelength resulting from the configuration of the wavelength selector.

18 Claims, 3 Drawing Sheets

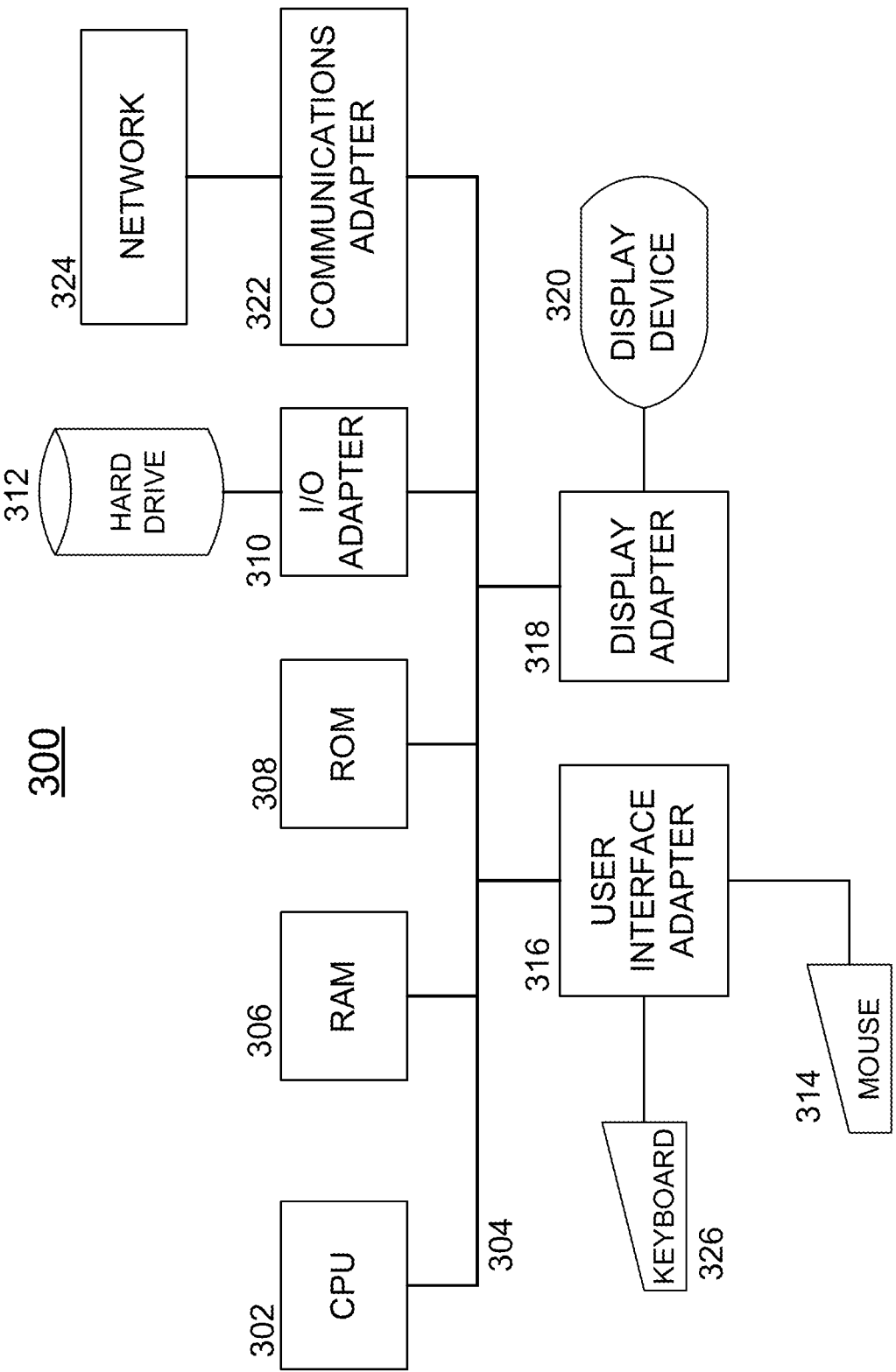

SYSTEM AND METHOD FOR ERROR CORRECTION IN A POLARIMETER

BACKGROUND OF THE INVENTION

The present invention relates in general to polarimeters, and more specifically to polarimeters that are used to measure optically active fluid samples.

An existing multiple wavelength polarimeter is shown in FIG. 1. A broadband light source 1 projects a beam of substantially parallel light through fixed polarizer 2. The light beam 21, which after passing through polarizer 2 consists of single-plane polarized components at various wavelengths, enters Faraday cell 3. Faraday cell 3, typically constructed of a transparent rod of suitable material arranged axially to the beam, is wound with a coil carrying an oscillating current transmitted by signal generator 4. The oscillating current signal causes the plane of polarization of the parallel-light beam to oscillate about the fixed direction established by polarizer 2 with an amplitude proportional to the current in the coil. The light beam 21 then passes through the optically active sample 24 contained in sample cell 5 (also referred to herein as container 5). The optical characteristics of the sample 24 generally impart additional rotation of the mean plane of polarization of the light beam 21 relative to the polarization of the beam established by fixed polarizer 2. The additional rotation imparted by the beam 21 passing through the sample may be proportional to the concentration of an optically active constituent in the sample 24 being measured. The term "optically active sample" is intended to include the case of a null or blank sample with an optical activity of zero, in addition to real samples which operate to change one or more characteristics of light beam 21.

Light beam 21 may then pass through analyzer 6. Analyzer 6 may include a polarizer mounted so as to be rotatable about the axis of the beam. The rotational position of the polarizer may be determined by controller 7 acting through the motor and encoder unit 8. The wavelength of interest can then be isolated by wavelength selector 9. Wavelength selector 9 may include a motorized monochromator or filter wheel. The intensity of the beam 21 arriving at the detector 10 is generally proportional to the square of the cosine of the angle between the beam polarization direction upon exit from sample cell 5 and the analyzer polarization direction.

Fourier analysis of the beam intensity variation with time determines the sign of the minimum angle separating (a) the beam polarization direction upon exit from sample cell 5 from the (b) analyzer 6 polarization direction that is needed in order to null the rotation of the sample. If this minimum angle is sufficiently small relative to the amplitude of the oscillating polarization produced by the Faraday cell 3, then the magnitude of the minimum angle can be determined as well.

Together, this sign and magnitude information is used to rotate the analyzer 6 to extinguish or "null" the component of intensity that is due to the rotation of polarization plane induced by the sample to be measured. The analyzer 6 angle needed to null the system in this manner, when no sample is present in sample container 5, becomes the zero reference. Any additional analyzer 6 angle needed to null the system when a sample 24 to be measured is present in container 5 constitutes a measurement of the optical rotation caused by the sample 24. This additional analyzer 6 angle (i.e. the analyzer angle over and above the angle needed to null the system when no sample is present in sample cell 5) may be proportional to the concentration of an optically active constituent in the sample 5 being measured.

In existing polarimeters of the type depicted in FIG. 1, one source of measurement error is the wavelength error of the wavelength selector 9. Commercially available compact monochromators intended for use in benchtop analytical instrumentation typically have a wavelength accuracy on the order of 1 nanometer (nm) and a wavelength repeatability of plus or minus 0.2 nm. If wavelength repeatability errors of this magnitude were present during optical rotation measurements of a normal sucrose solution at a wavelength of 589 nm at 20° C. (degrees Celsius), the contribution of this error source to the optical rotation repeatability would be about 0.025 degrees of rotation. This is much larger than the 0.002 degree rotation repeatability typically achieved by fixed-wavelength polarimeters. If the wavelength selector is a wheel or turret of discrete bandpass filters or if the wavelength is selected with a manually interchangeable bandpass filters, wavelength errors can also arise due to the temperature coefficient of the filters, the inclination of the filter to the beam path, or the degradation of the filter due to environmental conditions such as humidity or mechanical shock.

Accordingly, there is a need in the art to address the error that arises in polarimetry measurements.

SUMMARY OF THE INVENTION

According to one aspect, the present invention is directed to a polarimeter that may include a light source for transmitting a light beam through a sample within a container; a wavelength selector configured to specify a target wavelength at which the polarization rotation of the light beam emerging from the sample will be evaluated; a polarization rotator configured to be selectively moved into and out of a path of the light beam from the light source; and a detector for obtaining a first measurement of the light beam polarization rotation with the polarization rotator outside the path of the light beam, and a second measurement of the light beam polarization rotation with the polarization rotator within the path of the light beam, with both measurements occurring at the wavelength resulting from the configuration of the wavelength selector.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIG. 3 is a block diagram of a computer system useable in accordance with an embodiment of the present invention.

DETAILED DESCRIPTION OF THE PREFERRED EMBODIMENTS

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" or "in an embodiment" in various places in the specification do not necessarily all refer to the same embodiment.

Figure 1:
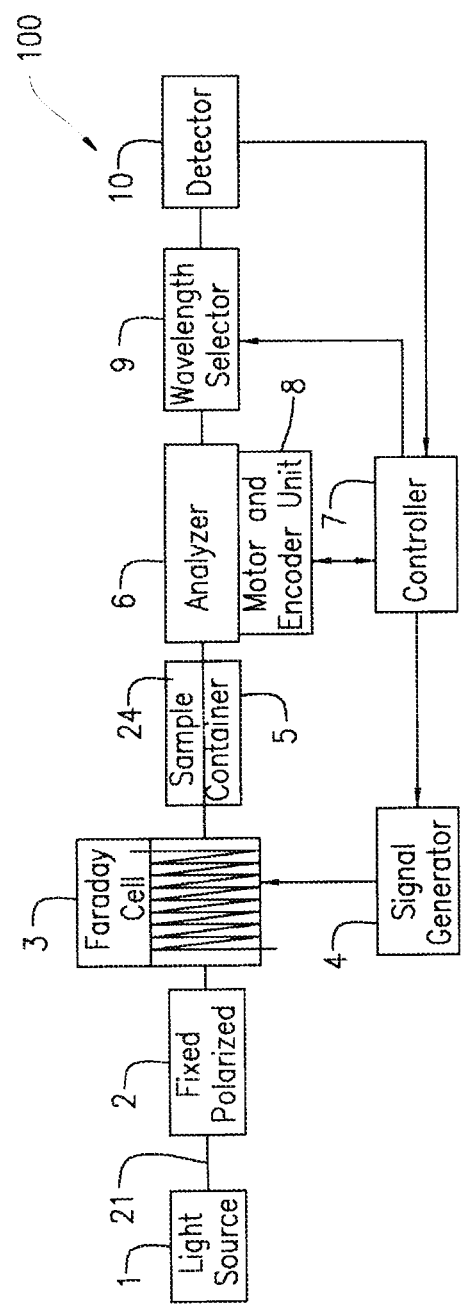
FIG. 1 is a block diagram of a polarimeter.
Figure 2:
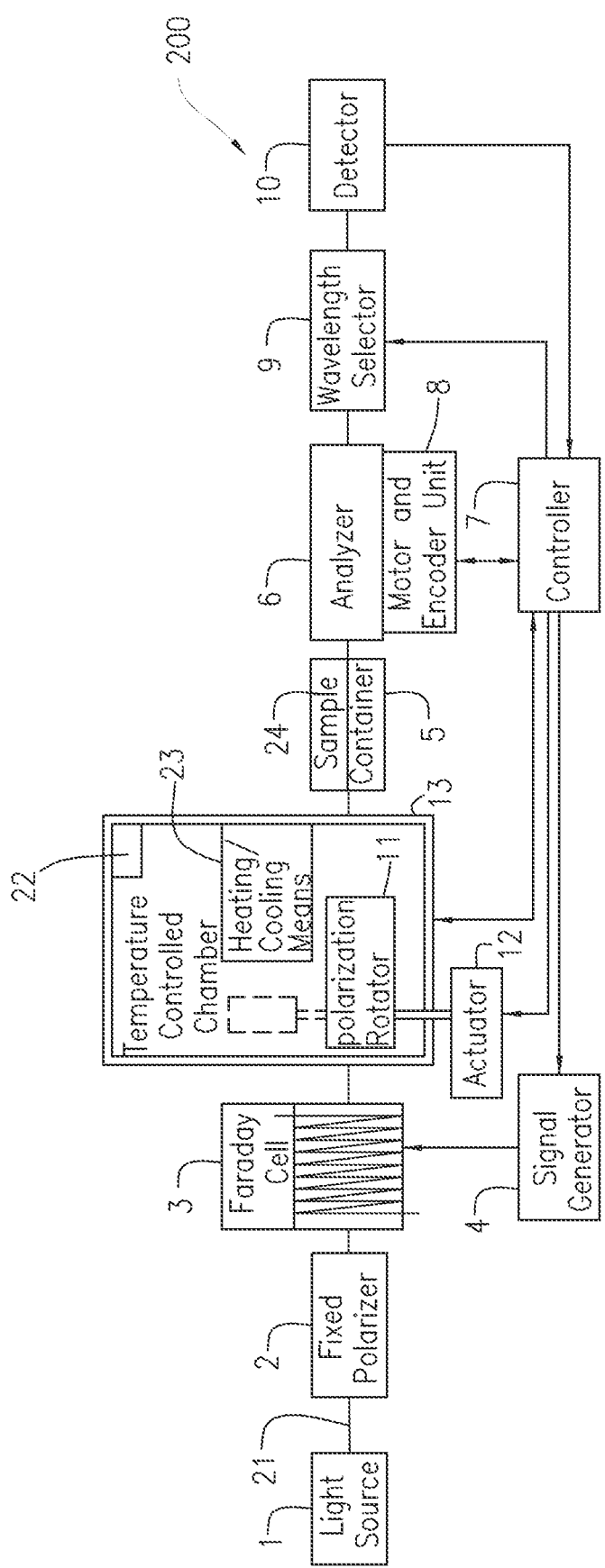
FIG. 2 is a block diagram of a polarimeter in accordance with an embodiment of the present invention.

The embodiments disclosed herein may be operable to provide apparatuses and methods for providing multiple wavelength polarimetry that incorporates the benefits of multiple wavelength measurement without incurring the wavelength errors that are present in existing wavelength selectors. An apparatus according to one embodiment of the present invention is shown in FIG. 2. In addition to the apparatus discussed in connection with FIG. 1, the apparatus 200 of FIG. 2 may further include an actuator 12 and/or a temperature controlled chamber 13 which may include a polarization rotator 11. Chamber 13 may further include temperature sensor 22 and/or heating/cooling means 23. Heating/cooling means 23 may include a resistance heater for heating purposes and may include an active refrigeration system for cooling purposes. However, other cooling and/or heating systems may be employed, and the invention is not limited to the heating and cooling apparatuses recited above.

In this embodiment, a broadband light source 1 may project a beam of substantially parallel light 21 through fixed polarizer 2. The light beam 21, which after passing through polarizer 2 preferably includes single-plane polarized components at various wavelengths, preferably enters Faraday cell 3. Preferably, Faraday cell 3 causes the plane of polarization of light beam 21 to oscillate about the fixed direction established by polarizer 2. Light beam 21 may then pass through polarization rotator 11 which may be moved into and out of the path of light beam 21 by actuator 12 in response to a signal from controller 7.

The polarization rotator 11 may be chosen such that its optical rotary dispersion, which corresponds to the variation of light-beam polarization rotation as a function of wavelength, is either (a) tabulated or (b) characterized by a known function. Polarization rotator 11 may include a planar optical crystal quartz window with the optic axis of the crystal perpendicular to the faces and parallel to the path of beam 21. However, polarization rotator 11 is not limited to having the above-described structure.

The optical rotary dispersion of such quartz rotators has been well characterized, for example by the International Commission for Uniform Methods of Sugar Analysis, as found in the Proceedings of the 22nd session, 1998, Page 211. Actuator 12 is preferably operable to rotate polarization rotator 11 into and out of the path of light beam 21. Thus, actuator 12 is preferably a rotary actuator, and may be powered electrically, pneumatically, hydraulically, or any combination of two or more of the foregoing mechanisms for power transmission. Alternatively, another type of actuator could be used, such as a linear actuator for moving polarization rotator 11 into and out of the path of light beam 21.

Because polarization rotation is typically also a function of temperature, the polarization rotator 11 may be substantially enclosed by temperature-controlled chamber 13 which may include a temperature sensor 22 and a means for heating and/or cooling 23 (variations of which are discussed above). If temperature effects on the polarization rotator 11 are well known, the heating and/or cooling means may be eliminated in favor of using the temperature sensor 22 reading to calculate a correction to the polarization rotation measured at detector 10. If the polarization rotator 11 is within the path of light beam 21, polarization rotator 11 may impart additional rotation of the mean plane of polarization of light beam 21 relative to the direction established by fixed polarizer 2. The light beam 21 then preferably passes through the optically active sample 24 in container 5. The optical characteristics of sample 24 in container 5 generally impart still further rotation of the mean plane of polarization of light beam 21.

As noted elsewhere herein, the additional rotation of the mean plane of polarization of light beam 21 may be proportional to the concentration of an optically active constituent in sample 24, in container 5, to be measured. Light beam 21 may then be transmitted on to analyzer 6 after passing through sample 24. Wavelength selection may then be conducted in wavelength selector 9. Measurement of the rotation of the polarization of light beam 21 may then be conducted using detector 10. Preferably, wavelength selection and/or measurement of the optical rotation of the polarization of light beam 21 may be conducted for (a) a situation in which polarization rotator 11 is not placed in the path of light beam 21; and (b) a situation in which polarization rotator 11 is placed in the path of light beam 21.

Methods of Use

A preferred method for using an embodiment of the above-discussed apparatus is discussed below. Two consecutive measurements of the optical rotation of sample 24 may be made at detector 10 to aid in determining any error in the wavelength setting being used for wavelength selector 9. In a first measurement, the polarization rotator 11 may be within the path of beam 21. In a second measurement, the polarization rotator 11 may be outside of the path of beam 21.

When the polarization rotator 11 is not within the path of light beam 21, the measured rotation of the polarization of the beam 21 after proceeding through sample 24 is as follows:

$$M_1 = S(\lambda) + \frac{\delta S}{\delta \lambda} \Delta \lambda. \tag{Eq. 1}$$

In Equation (1), the first term on the right-hand side is the rotation of the sample at the desired wavelength, λ (which is also referred to herein as the target wavelength). The second term on the right-hand side of equation (1) is the local slope of the optical rotary dispersion of sample 24 multiplied by the unknown wavelength error, Δλ.

When the polarization rotator 11 is moved into the beam path the measured optical rotation of the polarization of beam 21 increases to:

$$M_2 = M_1 + R(\lambda + \Delta\lambda) \tag{Eq. 2}.$$

In equation (2), $M_2$ is the measured polarization rotation of light beam 21 with polarization rotator 11 placed within the path of light beam 21. The expression λ+Δλ is the wavelength at which the measurement $M_2$ is taken, which is also referred to herein as the true wavelength and the correct wavelength. The true wavelength may differ from the target wavelength desired when configuring wavelength selector 9 by the extent of the wavelength error present in wavelength selector 9.

The term R(λ+Δλ) corresponds to the contribution of polarization rotator 11 (while in the path of light beam 21) to the total measured polarization rotation value $M_2$ as measured at detector 10. The term "R" in equation (2) is the optical rotary dispersion of polarization rotator 11 which denotes the variation of polarization rotation as a function of wavelength. As mentioned previously herein, the optical rotary dispersion may be either tabulated or characterized by a mathematical function.

With reference to the mathematical function referred to above, one exemplary dispersion equation for quartz polarization rotators is shown in equation (3). We note that the present invention is not limited to using the equation shown to relate polarization rotation to wavelength. The specific optical rotation, [α], in degrees of rotation per mm of quartz at 20° C. with wavelength, λ, in microns is:

$$[\alpha] = -0.1963657 + \frac{7.262667}{\lambda^2} + \frac{0.1171867}{\lambda^4} + \frac{0.0019554}{\lambda^6} \quad \text{(Eq. 3)}$$

We now proceed to solve for the true wavelength, as follows:

$$\lambda + \Delta\lambda = R^{-1}(M_2 - M_1) \quad \text{(Eq. 4).}$$

where $R^{-1}$ is now the inverse of the function which defines the rotation of the polarization rotator as a function of wavelength. Consistent with the above discussion of the meaning of "R", the function $R^{-1}$ may be applied to the quantity $M_2-M_1$ by conducting a lookup of tabulated data correlating polarization rotation to wavelength. Alternatively, a mathematical function corresponding to the inverse of the function denoted by "R" may be applied to the quantity $M_2-M_1$ to yield the true wavelength. Once the correct wavelength is determined using equation (4), we may now work to correct the value of the rotation of the polarization of light beam 21, denoted by the symbol $M_1$. Various options may be available for determining the true light beam 21 polarization rotation, which are discussed below.

Methods of Correcting Measurements Due to Wavelength Error

Using a first approach, the measured light beam polarization rotation may be treated as having occurred at the true wavelength, λ+Δλ, rather than at the desired wavelength (also known as the target wavelength), λ.

Using a second approach, if the optical rotary dispersion of the sample 24 is known or can be approximated, then the measured light beam polarization rotation may be corrected using the wavelength error.

Using a third approach, if the adjustment resolution of the wavelength selector 9 is sufficiently fine, the wavelength selection setting can be adjusted to cancel the wavelength error calculated in equation (4), and the rotation of the polarization of the light beam 21 may be measured again using the corrected wavelength, as set by wavelength selector 9, using the apparatus and methods discussed above. Once a correction has been determined at a particular wavelength, it can be also applied to subsequent light beam polarization rotation measurements, so long as the wavelength selector 9 remains at that wavelength.

Embodiments of the present invention preferably reduce or eliminate errors in measurements of light beam polarization rotation that are caused by wavelength errors that occur in existing wavelength selectors. Moreover, any error source may be corrected where there is a known relationship between the effect on the optically active sample and the effect on the polarization rotator. For example, for a fixed wavelength measurement, a known change in the quantity $(M_2-M_1)$ could be used as to correct the optical rotation measurement for any error that occurs in proportion to the value of the wavelength.

Reference herein to the use of a Faraday-modulated nulling polarimeter as the polarimeter of choice is for illustrative purposes only. The novel features disclosed herein may be applied to systems using other types of polarimeters such as but not limited to: non-modulated polarimeters; polarimeters with continuously rotating elements; photoelastic elements; and various other configurations.

FIG. 3 is a block diagram of a computing system 300 adaptable for use with one or more embodiments of the present invention. For instance, variations of computing system 300 may be included within devices in apparatus 200 such as but not limited to controller 7, signal generator 4, and/or detector 10. Additionally or alternatively, a computer system 300 (which may also be referred to as a processor) may be deployed in addition to the devices shown in FIG. 2, and may be used to conduct the computations associated with equation (1) through equation (4), which are shown earlier in this document. Such a separate computing device 300 is preferably placed in communication with detector 10 and/or other components of apparatus 200.

Central processing unit (CPU) 302 may be coupled to bus 304. In addition, bus 304 may be coupled to random access memory (RAM) 306, read only memory (ROM) 308, input/output (I/O) adapter 310, communications adapter 322, user interface adapter 306, and display adapter 318.

In an embodiment, RAM 306 and/or ROM 308 may hold user data, system data, and/or programs. I/O adapter 310 may connect storage devices, such as hard drive 312, a CD-ROM (not shown), or other mass storage device to computing system 300. Communications adapter 322 may couple computing system 300 to a local, wide-area, or global network 324. User interface adapter 316 may couple user input devices, such as keyboard 326, scanner 328 and/or pointing device 314, to computing system 300. Moreover, display adapter 318 may be driven by CPU 302 to control the display on display device 320. CPU 302 may be any general purpose CPU.

It is noted that the methods and apparatus described thus far and/or described later in this document may be achieved utilizing any of the known technologies, such as standard digital circuitry, analog circuitry, any of the known processors that are operable to execute software and/or firmware programs, programmable digital devices or systems, programmable array logic devices, or any combination of the above. One or more embodiments of the invention may also be embodied in a software program for storage in a suitable storage medium and execution by a processing unit.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of polarimetry, comprising:
providing a polarimeter including a light source;
transmitting a light from the light source beam through a sample in a container in the polarimeter;
obtaining a first measurement of polarization rotation of the light beam passing through the sample, using a target wavelength setting of a wavelength selector in said polarimeter;
inserting a polarization rotator into a path of the light beam of said polarimeter;
obtaining a second measurement of the polarization rotation of the light beam, after the light beam has passed through both the polarization rotator and the sample; and
calculating a true wavelength at which the first and second polarization rotation measurements were obtained from the first and second polarization rotation measurements and from a value of optical rotary dispersion of the polarization rotator.

2. The method of claim 1 further comprising:
adjusting the target wavelength setting, of the wavelength selector, to compensate for a wavelength error quantity separating the target wavelength and the calculated true wavelength, thereby canceling an effect of the wavelength error quantity.

3. The method of claim 2 further comprising:
conducting a polarimeter reading of the sample in the container at the adjusted target wavelength setting.

4. The method of claim 1 further comprising:
conducting a polarimeter reading of the sample in the container using the target wavelength setting of the wavelength selector; and associating the polarimeter reading with the calculated true wavelength.

5. The method of claim 1 further comprising:
conducting a raw light beam polarization rotation reading of the sample in the container using the target wavelength setting for the wavelength selector; and calculating a corrected reading of the light beam polarization value of the sample from the raw light beam polarization rotation value and a value of an optical rotary dispersion of the sample.

6. The method of claim 5 further comprising:
applying the light beam polarization rotation reading correction calculation to subsequent measurements of samples using said target wavelength setting in said wavelength selector.

7. A polarimeter comprising:
a polarized light source for transmitting a polarized light beam through a sample within a container;
a polarizer that polarizes the light beam emerging from the sample;
a wavelength selector configured to specify a target wavelength at which the polarization rotation of the light beam emerging from the polarizer will be evaluated;
a polarization rotator configured to be selectively moved into and out of a path of the light beam from the light source;
a detector for obtaining a first measurement of the light beam polarization rotation of the sample with the polarization rotator outside the path of the light beam, and a second measurement of the light beam polarization rotation of the sample with the polarization rotator within the path of the light beam, with both said measurements occurring at the wavelength resulting from the configuration of the wavelength selector; and
a processor that calculates a true wavelength at which the first and second polarization rotation measurements were obtained, from the first and second polarization rotation measurements and from a value of optical rotary dispersion of the polarization rotator.

8. The polarimeter of claim 7 wherein the polarization rotator is a crystal quartz rotator.

9. The polarimeter of claim 7 wherein the polarization rotator is incorporated within a temperature controlled chamber.

10. The polarimeter of claim 9 wherein the temperature controlled chamber includes a temperature sensor located therein.

11. the polarimeter of claim 9 wherein the temperature controlled chamber includes at least one of:
a heating means; and a cooling means.

12. The polarimeter of claim 7 further comprising:
an actuator for moving the polarization rotator either into or out of the path of the light beam upon.

13. The polarimeter of claim 12 further comprising:
a controller for providing positioning instructions to the actuator for positioning the polarization rotator.

14. The polarimeter of claim 7 wherein the wavelength selector comprises:
a monochromator for selecting a target wavelength.

15. The polarimeter of claim 7 wherein the wavelength selector comprises at least one bandpass filter.

16. The polarimeter of claim 7 wherein the polarimeter is further operable to:
calculate a correction to the first obtained measurement of polarization rotation using the calculated true wavelength.

17. The polarimeter of claim 7 wherein the polarimeter is operable to
adjust the target wavelength setting, in the wavelength selector, to compensate for a wavelength error quantity separating the target wavelength and the calculated true wavelength, thereby canceling an effect of the wavelength error quantity.

18. A method of polarimetry comprising:
providing a polarimeter including a light source;
transmitting a light from the light source beam through a sample in a container in the polarimeter;
obtaining a first measurement of polarization rotation of the light beam passing through the sample, using a target wavelength setting of a wavelength selector in said polarimeter;
inserting a polarization rotator into a path of the light beam of said polarimeter;
obtaining a second measurement of the polarization rotation of the light beam, after the light beam has passed through both the polarization rotator and the sample; and
identifying an operational variable within the polarimeter that impacts both the polarization rotator and the sample;
determining a value of the operational variable during the second measurement of the polarization rotation from the difference between the first and second polarization rotation measurements and from a correlation between the characteristics of the polarization rotator and values of the operational variable; and
determining an actual value of the operational variable within the polarimeter during the first measurement of the polarization rotation from the value of the operational value determined to be present during the second measurement of the polarization rotation and a relationship between the value of polarization rotation of the sample and the value of the operational variable.

* * * * *